(12) United States Patent
Petersen et al.

(10) Patent No.: US 9,733,799 B2
(45) Date of Patent: *Aug. 15, 2017

(54) CENTRAL STATION INTEGRATION OF PATIENT DATA

(71) Applicant: Welch Allyn, Inc., Skaneateles Falls, NY (US)

(72) Inventors: Eric G. Petersen, Beaverton, OR (US); John H. Irwin, Marcellus, NY (US); Robert P. Wilmington, Vancouver, WA (US); Sean M. Kelley, Tualatin, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 341 days.

This patent is subject to a terminal disclaimer.

(21) Appl. No.: 14/487,667

(22) Filed: Sep. 16, 2014

(65) Prior Publication Data

US 2015/0007098 A1 Jan. 1, 2015

Related U.S. Application Data

(63) Continuation of application No. 13/440,698, filed on Apr. 5, 2012, now Pat. No. 8,874,379.

(51) Int. Cl.
*G01N 33/48* (2006.01)
*G06F 3/0482* (2013.01)
*G06F 19/00* (2011.01)
*G06F 3/0484* (2013.01)
*G06F 3/0488* (2013.01)

(52) U.S. Cl.
CPC .......... *G06F 3/0482* (2013.01); *G06F 3/0488* (2013.01); *G06F 3/04842* (2013.01); *G06F 19/3418* (2013.01)

(58) Field of Classification Search
CPC .................................................. G06F 3/0482
USPC ........................................................... 702/19
See application file for complete search history.

(56) References Cited

U.S. PATENT DOCUMENTS

| 7,396,330 | B2 | 7/2008 | Banet et al. |
|---|---|---|---|
| 2001/0014769 | A1 | 8/2001 | Bufe et al. |
| 2004/0111045 | A1 | 6/2004 | Sullivan et al. |
| 2005/0021370 | A1 | 1/2005 | Riff et al. |
| 2005/0055242 | A1 | 3/2005 | Bello et al. |
| 2005/0197860 | A1 | 9/2005 | Joffe et al. |
| 2006/0200009 | A1 | 9/2006 | Wekell et al. |
| 2007/0168222 | A1 | 7/2007 | Hoyme et al. |
| 2007/0179811 | A1 | 8/2007 | Reiner |
| 2008/0300919 | A1 | 12/2008 | Charlton et al. |
| 2009/0182575 | A1 | 7/2009 | Warner et al. |
| 2010/0030575 | A1 | 2/2010 | Patel et al. |
| 2010/0261977 | A1 | 10/2010 | Seely |
| 2011/0001605 | A1 | 1/2011 | Kiani et al. |
| 2011/0227739 | A1 | 9/2011 | Gilham et al. |
| 2011/0245630 | A1 | 10/2011 | St. Pierre et al. |
| 2011/0306926 | A1 | 12/2011 | Woo |

FOREIGN PATENT DOCUMENTS

WO   03098908 A1   11/2003

OTHER PUBLICATIONS

International Search Report and Written Opinion in PCT/US2013/031421, mailed Jun. 12, 2013, 12 pages.
Managing Patient Context for Bedside Medical Devices—Today's Situation, posted by Brian McAlpine in Connectivity, accessed at: http://medicalconnectivity.com/2008/12/09/managing-patient-context-for-bedside-medical-devices-todays-situation/, on Dec. 9, 2008, 8 pages.
Patient Monitoring in Intensive Care Unit and Critical Care Unit accessed at: http://www.newtech-medical.com/articles/Patient-Monitoring-in-Intensive-Care-Unit-and-Critical-Care-Unit.html, on Feb. 16, 2012, 4 pages.
Wargitch et al., An Organizational-Memory-Based Approach for an Evolutionary Workflow Management System—Concepts and Implementation, System Sciences, proceedings of the Thirty-First Hawaii International Conference, vol. 1, issued Jan. 6-9, 1998, pp. 174-183.

*Primary Examiner* — Jerry Lin
(74) *Attorney, Agent, or Firm* — Merchant & Gould P.C.

(57) ABSTRACT

A method for displaying medical data includes receiving physiological data from a first medical monitoring device. The physiological data is obtained on a continuous basis. Physiological data is received from a second medical monitoring device. The physiological data from the second medical monitoring device is obtained on a non-continuous basis. The physiological data received from the first medical monitoring device and the physiological data received from the second medical monitoring device are displayed on a central display station. The central display station is located centrally within a care unit of a caregiving facility.

18 Claims, 15 Drawing Sheets

900↘
902

Patient Review - Griffith, Tracie Leola  102B

| Flow Sheet | Continuous Trends | Patient Alarms |

27  6  69

History 904 | Timespan 906 | Interval 908
Last 24 hours ▽ | 8 hour span ▽ | Every 15 minutes ▽
916

Monday 03/05/2012 | Tuesday 03/06/2012
:00  18:00  20:00  22:00 | 02:00  04:00  06:00  08:00  10:00  12:00  14:00

| 910 | 912—Confirmed | TEMP °F | NIBP mmHg | PR BPM | RR bpm | SpO2 % | etCO2 mmHg | IPI | SpHb g/dL | PAIN |
|---|---|---|---|---|---|---|---|---|---|---|
| Tue 03/06 15:58:04 | | | | 60 | 47 | 92 | 57 | 8 | 14.0 | |
| Tue 03/06 15:56:02 | | 106.0 | 225/115 | 125 | 48 | 105 | 580 | 9 | 22.0 | 10 |
| Tue 03/06 15:51:02 | | 99.0 | 216/107 | 60 | 47 | 92 | 570 | 8 | 14.0 | 10 |
| Tue 03/06 15:46:44 | | | | 46 | -1 | 86 | 11 | 8 | 3.0 | |
| Tue 03/06 15:46:43 | | | | 60 | 47 | 92 | 57 | 8 | 14.0 | |
| Tue 03/06 15:46:02 | | 99.0 | 216/107 | 61 | 48 | 93 | 580 | 9 | 15.0 | 10 |
| Tue 03/06 15:41:02 | | 99.0 | 216/107 | 61 | 48 | 93 | 580 | 9 | 15.0 | 10 |
| Tue 03/06 15:36:02 | | 99.0 | 216/107 | 60 | 47 | 92 | 570 | 8 | 14.0 | 10 |
| Tue 03/06 15:31:45 | | 99.7 | 137/96 | 63 | | | | | 0.2 | |
| Tue 03/06 15:30:00 | | | | | | | | | | |
| Tue 03/06 15:29:45 | | 96.3 | 105/81 | 71 | | | | | 0.1 | |
| Tue 03/06 15:27:45 | | 96.3 | 105/81 | 71 | | | | | 0.1 | |
| Tue 03/06 15:25:45 | | 96.4 | 130/92 | 63 | | | | | 0.1 | |
| Tue 03/06 15:23:45 | | 98.3 | 136/77 | 71 | | | | | 0.1 | |
| Tue 03/06 15:21:45 | | 98.5 | 136/77 | 71 | | | | | 0.1 | |
| Tue 03/06 15:19:45 | | 98.5 | 108/62 | 92 | | | | | 0.2 | |
| Tue 03/06 15:15:00 | | | | | | | | | | |
| Tue 03/06 15:00:00 | | | | | | | | | | |
| Tue 03/06 14:45:00 | | | | | | | | | | |

| Patient Review - 101A - Carey, Manuela Joy | | | |
|---|---|---|---|
| Flow Sheet | Continuous Trends | Patient Alarms | |

1002

| Level | Date and Time | Duration | Event |
|---|---|---|---|
| ▲ | Wed 03/21 14:09:49 | :31 | $CO_2$ End Tidal Lower Alarm |
| ▲ | Wed 03/21 14:09:49 | :31 | $CO_2$ IPI Lower Alarm |
| ▲ | Wed 03/21 14:09:49 | :31 | Saturation Lower Alarm |
| ▲ | Wed 03/21 14:09:49 | :31 | HR PR Lower Alarm |
| ▲ | Wed 03/21 14:09:49 | :31 | Respiration Lower Alarm |
| ▲ | Wed 03/21 14:09:49 | :31 | 5pHB Lower Alarm |
| ▲ | Wed 03/21 14:09:49 | :30 | Saturation Lower Alarm |
| ▲ | Wed 03/21 14:03:31 | n/a | NIBP LowAlarmTriggered |
| ▲ | Wed 03/21 14:03:31 | :01 | Temerature Lower Alarm |
| ▲ | Wed 03/21 14:03:31 | :01 | Diastolic Lower Alarm |
| ▲ | Wed 03/21 14:03:31 | :01 | Systolic Lower Alarm |
| ▲ | Wed 03/21 14:03:31 | n/a | TEMP LowAlarm Triggered NIBP LowAlarmTriggered |
| ▲ | Wed 03/21 13:50:31 | n/a | NIBP LowAlarmTriggered |
| ▲ | Wed 03/21 13:53:31 | n/a | NIBP LowAlarmTriggered |
| ▲ | Wed 03/21 13:40:31 | n/a | NIBP LowAlarmTriggered |
| ▲ | Wed 03/21 13:43:31 | n/a | NIBP LowAlarmTriggered |
| ▲ | Wed 03/21 13:39:18 | :30 | HR PR Upper Alarm |
| ▲ | Wed 03/21 13:39:18 | :30 | Respiration Upper Alarm |
| ▲ | Wed 03/21 13:39:18 | :30 | $CO_2$ End Tidal Upper Alarm |
| ▲ | Wed 03/21 13:39:18 | :301 | $CO_2$ Fraction Inspired Upper Alarm |
| ▲ | Wed 03/21 13:39:18 | :30 | SpHB Upper Alarm |
| ▲ | Wed 03/21 13:39:18 | :31 | $CO_2$ Fraction Incurred Upper Alarm |

FIG. 10

CENTRAL STATION INTEGRATION OF PATIENT DATA

CROSS-REFERENCE TO RELATED APPLICATIONS

The present application claims priority to U.S. Non-Provisional Patent Application Ser. No. 13/440,698, filed Apr. 5, 2012 and titled "Central Station Integration of Patient Data", which is hereby incorporated by reference in its entirety.

BACKGROUND

In a medical setting, patient data may be obtained via various workflows. In one workflow, physiological sensor devices are physically attached to a patient and patient data is continually monitored from the physiological sensor devices. In another workflow, spot or episodic data is obtained from a patient, typically by a nurse or other clinician at intervals dictated by the workflow and by an acuity level for each patient.

Patient data obtained on a continuous basis is commonly displayed on a central display station so that clinicians can easily view vital signs being monitored for the patient. Patient data obtained on a spot or episodic basis is often manually entered on a patient chart or stored in a computer system. Clinicians needing to view both patient data obtained on a continuous basis and patient data obtained on a spot or episodic basis often need to access multiple computer systems, display stations or documents in order to view both types of patient data.

SUMMARY

Embodiments of the disclosure are directed to systems and methods for displaying medical data. Physiological data is received from a first medical monitoring device. The physiological data is obtained on a continuous basis. Physiological data is received from a second medical monitoring device. The physiological data from the second medical monitoring device is obtained on a non-continuous basis. The physiological data received from the first medical monitoring device and the physiological data received from the second medical monitoring device are displayed on a central display station. The central display station is located centrally within a care unit of a caregiving facility.

The details of one or more techniques are set forth in the accompanying drawings and the description below. Other features, objects, and advantages of these techniques will be apparent from the description, drawings, and claims.

DESCRIPTION OF THE DRAWINGS

FIG. 9 shows another screen shot of an example patient review screen.

FIG. 10 shows a screen shot of a patient alarms screen.

DETAILED DESCRIPTION

The present disclosure is directed to a system and methods for integrating continuous and episodic data from a patient at a central display station.

In example embodiments, the central display station receives patient data from one or more monitoring devices that receive continuous physiological data for the patient. The central display station also receives patient data from one or more spot or episodic devices that obtain physiological data from the patient from spot or episodic monitoring devices, for example a portable vital signs measurement device. The continuous physiological data and the episodic physiological data are integrated and displayed at the central display station.

The central display station is typically located at a central location within a care unit of caregiving facility (e.g., hospital or clinic), for example at a central nurse's station, so that the physiological data may be easily viewed by clinicians. A care unit is an area of the caregiving facility in which patients are treated and monitored. In example embodiments, a caregiving facility may have one or more central display stations located at hubs or nurses areas in care units throughout the facility so that caregivers can easily access the central display stations to monitor multiple patients at once. In this disclosure, episodic physiological data refers to physiological data obtained on a non-continuous basis. In this disclosure, the terms "episodic" and "spot" are used interchangeably.

Figure 1:
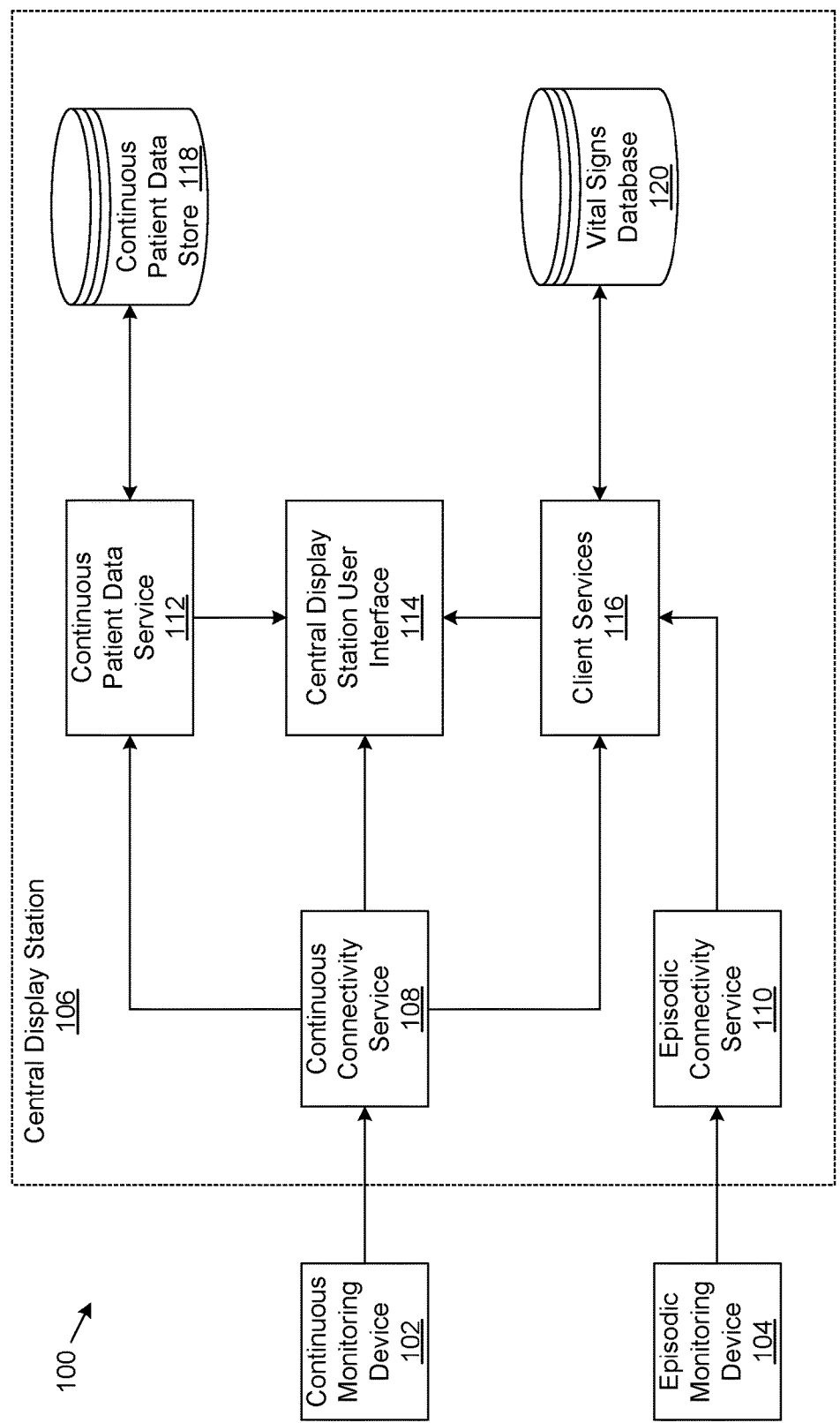
FIG. 1 shows an example system that supports integration of continuous and episodic physiological data for a patient at a central display station.

FIG. 1 shows an example system 100 that supports integration of continuous and episodic physiological data for a patient at a central display station. The system 100 includes a continuous monitoring device 102, an episodic monitoring device 104, and a central display station 106.

The continuous monitoring device 102 may be physically connected to the central display station 106 or may be connected to the central display station 106 via a wireless connection. The episodic monitoring device 104 is typically connected to the central display station 106 via a wireless connection. More than one continuous monitoring device 102 and episodic monitoring device 104 may be used.

The example continuous monitoring device 102 is a monitoring device that receives physiological data from a patient on a continuous basis, typically at millisecond intervals. Continuous physiological data is typically obtained for acute patients, for example from surgical patients or from post-surgical patients in an intensive care unit. Examples of continuous physiological data include blood pressure, temperature, pulse rate, oxygen saturation level (SPO2), end tidal carbon dioxide (ETCO2) and respiratory rate. Other types of physiological data are possible. The physiological data is typically displayed on the continuous monitoring device 102, which is typically located near the patient. An example of a continuous monitoring device is the Welch Allyn 1500 Patient Monitor from Welch Allyn, Inc. of Skaneateles Falls, N.Y.

The example episodic monitoring device 104 is a monitoring device that receives physiological data from a patient on an episodic or spot basis. Episodic data is typically obtained for less acute patients, for example a patient recovering from surgery but out of intensive care. For these patients, physiological data may be obtained via a vital signs device that may be manually operated by a clinician, for example by a nurse or a certified nursing assistant (CNA). Examples of episodic data obtained from the vital signs device include blood pressure, temperature, pulse rate and SPO2. Other examples of episodic data are possible. Episodic data such as blood pressure, temperature, pulse rate and SPO2 may also be obtained on a continuous basis. However, when this data is obtained at specified intervals, for example when a nurse manually takes a patient's blood pressure and temperature, the data is designated as episodic data. For example, a nurse may manually obtain an oxygen saturation reading by manually clipping an SPO2 sensor to the patient and monitoring the SPO2 via a vital signs device. An example vital signs device is the Connex® Vital Signs Monitor from Welch Allyn, Inc. of Skaneateles Falls, N.Y. Intervals are typically specified by physician orders or care unit protocols.

The example central display station 106 includes a continuous connectivity service module 108, an episodic connectivity service module 110, a continuous patient data service module 112, a central display station user interface 114, a client services module 116, a continuous patient data store 118 and a vital signs database 120. In examples, the continuous patient data store 118 and the vital signs database 120 may be stored on databases external to the central display station 106.

As shown in FIG. 1, physiological data from the continuous monitoring device 102 is processed by continuous connectivity service module 108. The example continuous connectivity service module 108 provides connectivity services for continuous monitoring of devices such as the continuous monitoring device 102. Example connectivity services provided by the continuous connectivity service module 108 include receiving and routing continuous physiological data for a patient to application software for displaying the continuous physiological data on user interface 114 of the central display station and for storing the continuous physiological data in a continuous patient data store 118 and in a vital signs database 120.

Physiological data from the episodic monitoring device 104 is processed by episodic connectivity service module 110. The example episodic connectivity service module 110 provides connectivity services for episodic monitoring devices such as the episodic monitoring device 104. Example connectivity services provided by the episodic connectivity service module 110 includes routing episodic physiological data for a patient to application software for displaying the episodic physiological data on user interface 114 of the central display station and for storing the episodic physiological data in the vital signs database 120.

The example continuous patient data service module 112 is an application programming interface (API) used by the continuous connectivity service module 108 to store continuous physiological data for the patient in the continuous patient data store 118. API commands from the continuous connectivity service module 108 are used to store the continuous physiological data for the patient in the continuous patient data store 118. In addition, as explained later herein, API commands from the continuous patient data service module 112 are used to retrieve continuous patient data from the continuous patient data store 118 and provide the continuous patient data to central display station user interface 114.

The example central display station user interface 114 provides a user interface for the central display station. The user interface includes a plurality of display tiles that display physiological information for patients, as explained in more detail later herein.

The example client services module 116 provides support for storage, retrieval and modification of data entries, including, but not limited to patients, visits, episodic tests, user accounts and device connections. Access to the client services module 116 is via APIs typically provided by a dynamic link library (DLL), referred to as a client framework, not shown in FIG. 1.

The example continuous patient data store 118 is a repository for physiological data received from continuous monitoring device 102 and from other continuous monitoring devices. The physiological data stored in the continuous patient data store 118 can be later retrieved for detailed display on the user interface of the central display station 106.

The example vital signs data base 120 is a repository for physiological data received from episodic monitoring device 104 and from other episodic monitoring devices. The physiological data stored in the vital signs database 120 can be later retrieved for detailed display on the user interface of the central display station 106.

Figure 2:
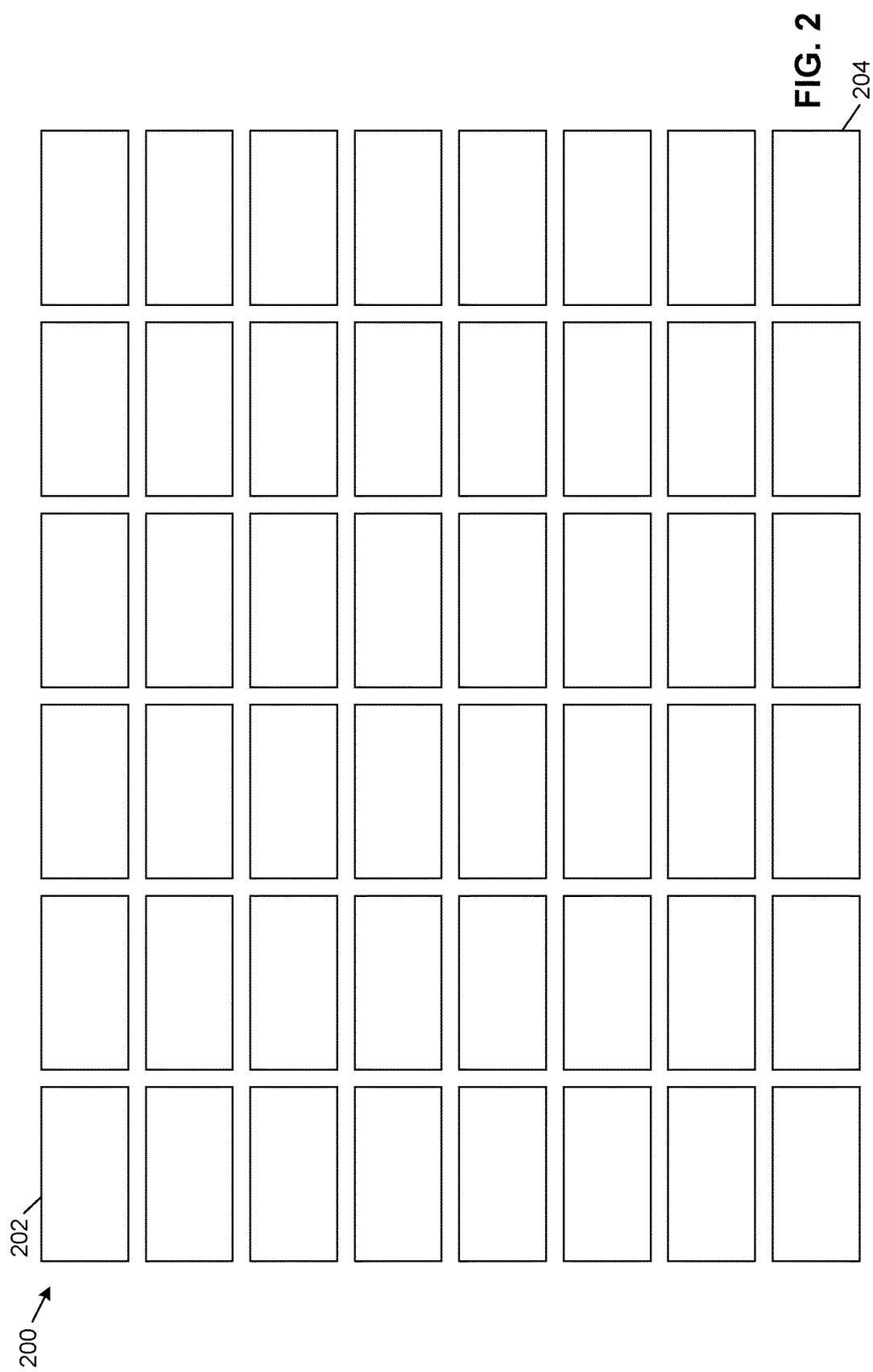
FIG. 2 shows an example user interface of the central display station of FIG. 1.

FIG. 2 shows an example user interface display 200, as provided by the central display station user interface 114. The user interface display 200 includes a plurality of display tiles 202-204. Each of the display tiles 202-204 provides a display of physiological data for a patient. Typically, each of the display tiles 202-204 displays physiological data for a different patient. The physiological data can include both continuous physiological data and episodic physiological data. The example user interface display 200 includes 36 display tiles, organized into six rows of six display tiles each. Other example display tile configurations include 24 display tiles organized into four rows of six display tiles each and 48 display tiles organized into eight rows of six display tiles each. Other configurations of display tiles are possible.

Figure 3:
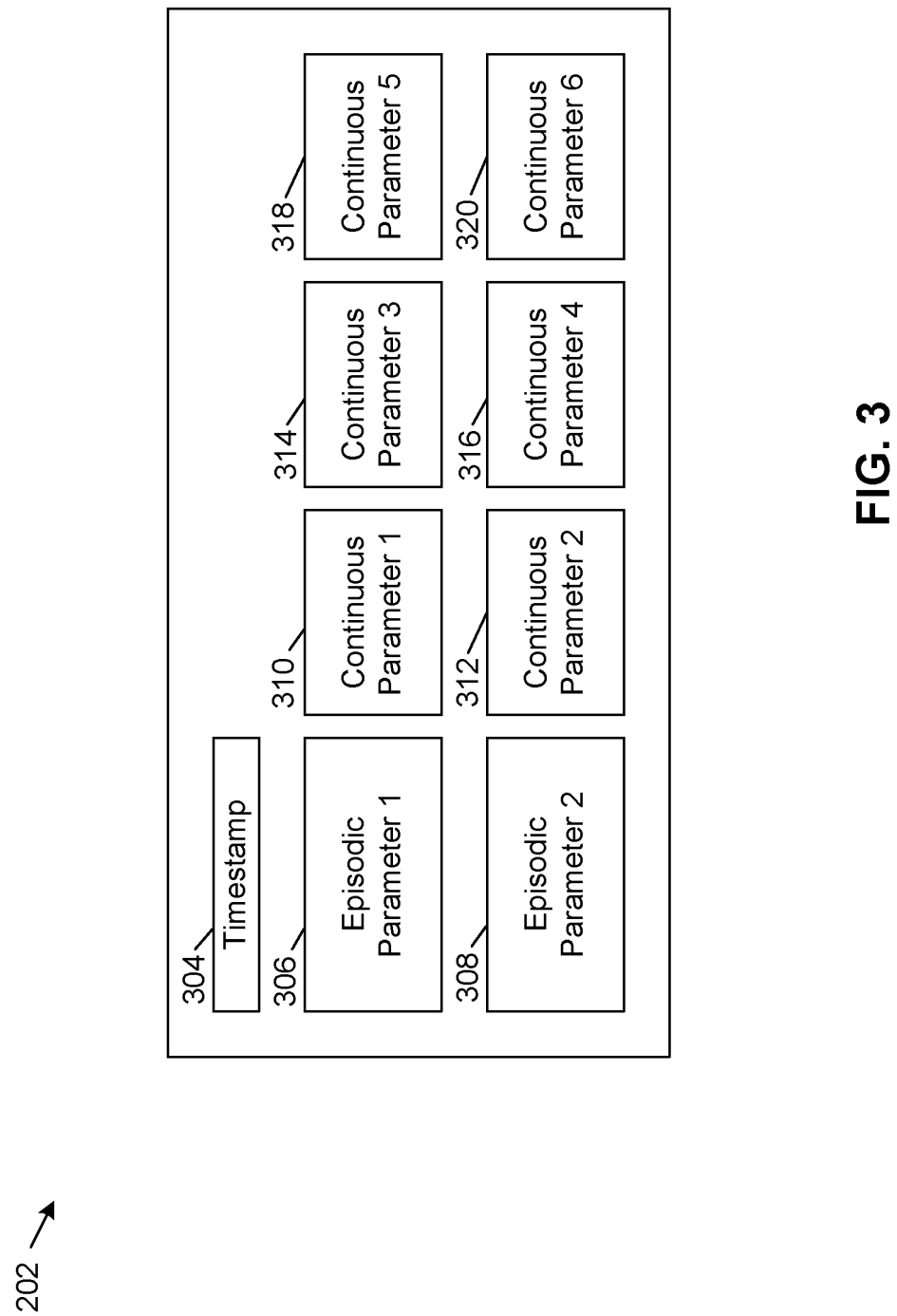
FIG. 3 shows an example layout for a display tile of the user interface of FIG. 2.

FIG. 3 shows the example display tile 202 in more detail. The display tile 202 displays physiological data for one patient. The display tile 202 includes a timestamp 304, episodic parameters 306, 308 and continuous parameters 310-320. The continuous parameters 310-320 are updated on a continuous basis, typically at one second intervals. The timestamp 304 displays a timestamp indicating when the episodic parameters 306, 308 were last updated. The episodic parameters 306, 308 display episodic physiological data, for example non-invasive blood pressure (NIBP) and temperature. Each episodic parameter 306, 308 displays physiological data for a different episodic parameter. The continuous parameters 310-320 display continuous physiological data, for example respiration rate and oxygen saturation (SPO2).

Figure 4:
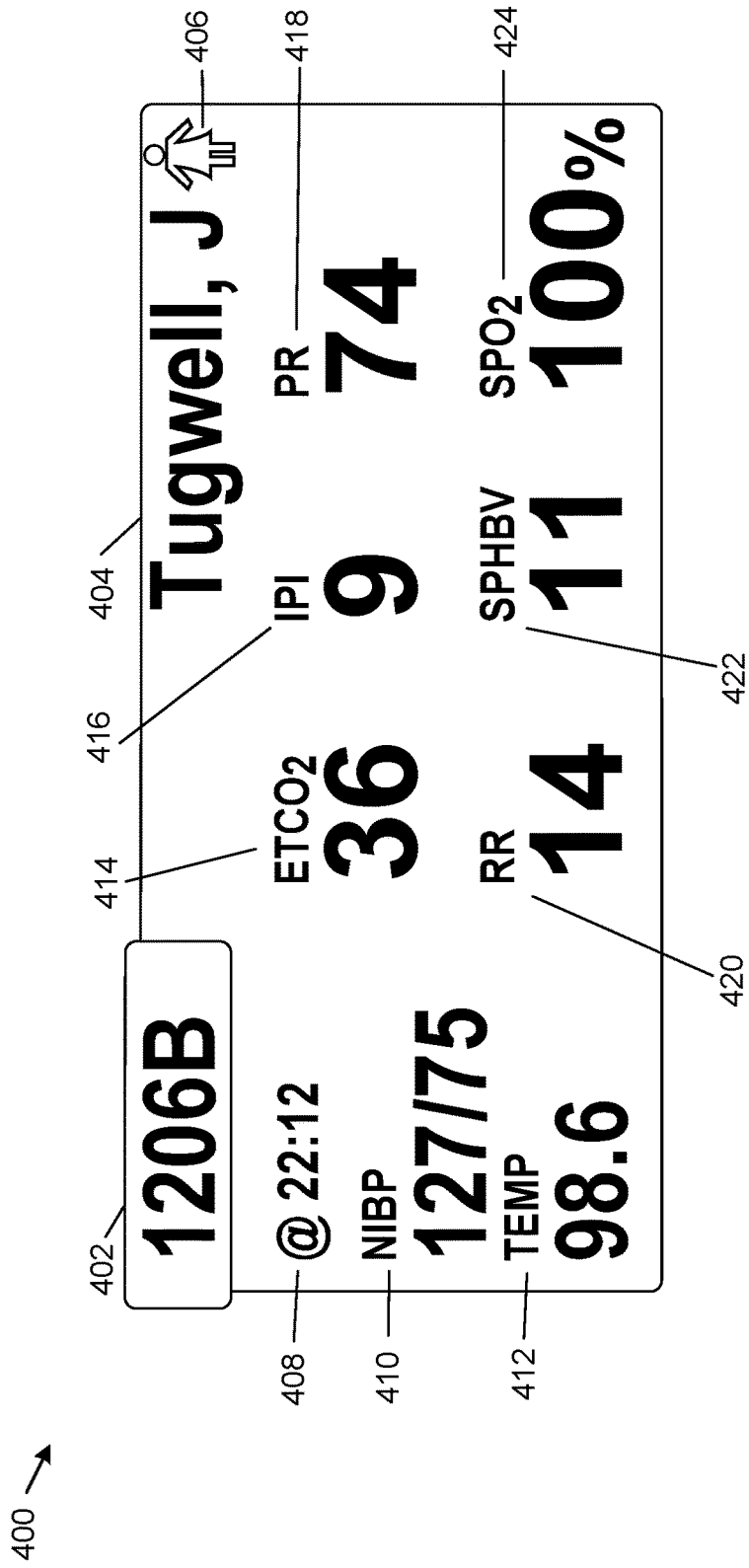
FIG. 4 shows an example screen shot for a display tile.

FIG. 4 shows an example screen shot of a display tile 400 corresponding to display tile 202. The display tile 400 includes a room identifier 402 for the patient, a name of the patient 404, an icon 406 representing the sex of the patient, a timestamp 408, episodic parameter 410 corresponding to non-invasive blood pressure, episodic parameter 412 corresponding temperature, continuous parameter 414 corresponding to end-tidal carbon dioxide (ETCO2), continuous parameter 416 corresponding to an integrated pulmonary index (IPI), continuous parameter 418 corresponding to pulse rate (PR), continuous parameter 420 corresponding to respiration rate (RR), continuous parameter 422 corresponding to venous calibrated total hemoglobin (SPHBV) and continuous parameter 424 corresponding to oxygen saturation (SPO2). Other episodic and continuous parameters are possible.

Figure 5:
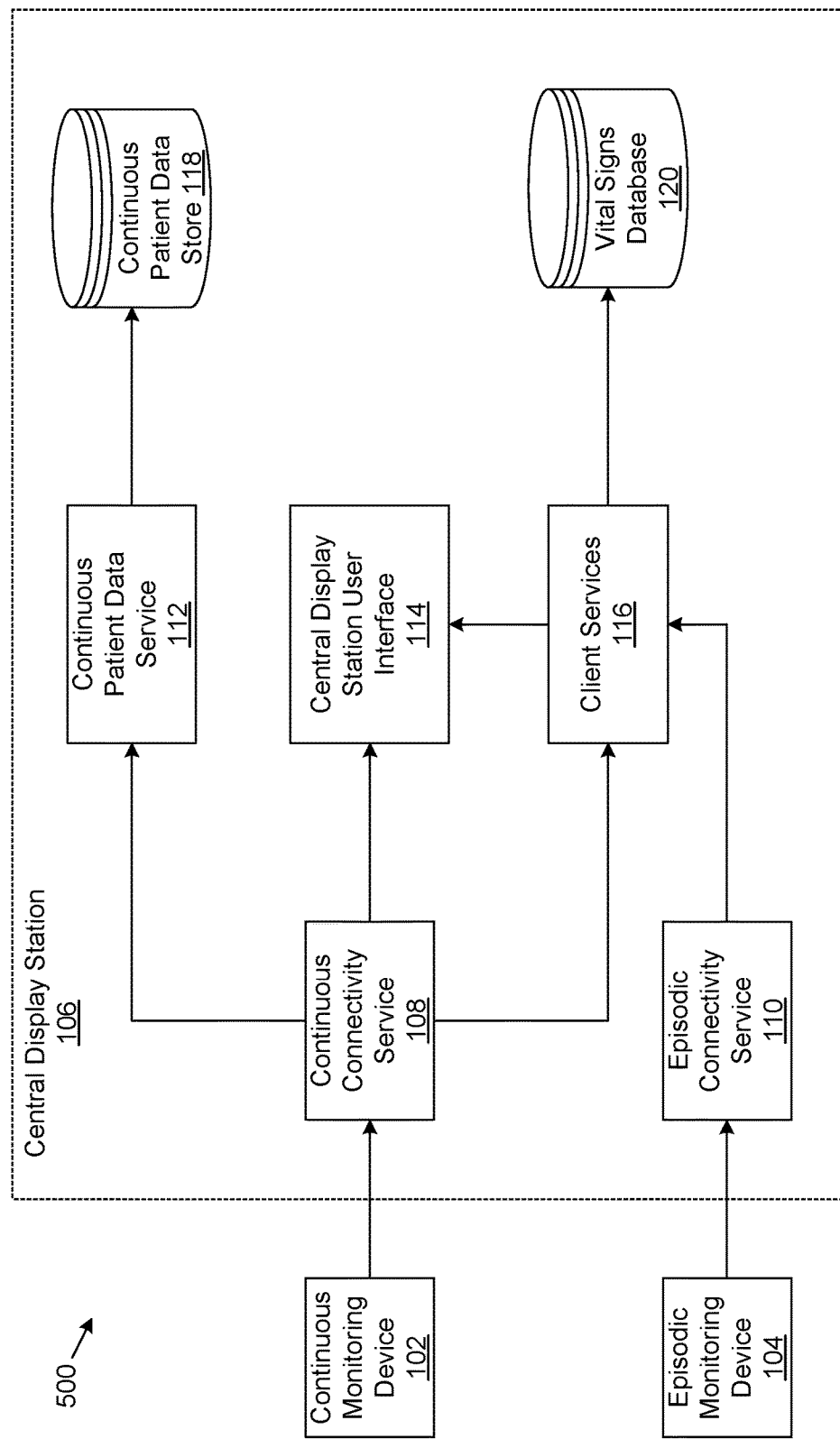
FIG. 5 shows components of the example system of FIG. 1.

FIG. 5 shows an example system 500 that includes components of the system 100 of FIG. 1 used in a data acquisition aspect of system 100 for obtaining and storing continuous and episodic data for a patient. In the example system 500, physiological data obtained on a continuous basis for a patient is sent to the continuous connectivity service module 108. The continuous connectivity service module 108 sends the continuous physiological data for the central display station user interface 114 for display on a display tile, for example display tile 202, of the user interface 200 of the central display station 106. The continuous connectivity service module 108 also sends the continuous physiological data for the patient to the continuous patient data service module 112. The continuous connectivity service module 108 also sends episodic data collected from a continuous device to the vital signs database 120 using client services 116, as discussed later herein.

The continuous connectivity service module 108 uses one or more API commands to send the continuous physiological data for the patient to the continuous patient data service module 112. The continuous patient data service module 112 uses file system API commands to store the continuous physiological data for the patient in the continuous patient data store 118.

The continuous connectivity service module 108 also sends the continuous physiological data for the patient to client service module 116. The client service module 116 uses API commands, typically SQL commands, to store the continuous physiological data in the vital signs database 120. As discussed, the vital signs database 120 stores episodic physiological data for a patient. However, some physiological data collected from a continuous device may also include episodic type data. For example, pulse rate may be obtained on an episodic basis when a nurse or CNA makes rounds and manually obtains the pulse rate of a patient. However, pulse rate is also obtained during the process of measuring oxygen saturation (SPO2). Because pulse rate data is available from the measurement of SPO2, that pulse rate data is also stored in the vital signs database 120.

As another example, NIBP may be measured manually by a nurse or CNA but may also be automatically taken at intervals, for example when an automatic blood pressure machine is connected to the patient. Pulse rate is typically obtained by automatic blood pressure machines when measuring blood pressure. The pulse rate obtained on an interval basis by the automatic blood pressure machine is stored in the vital signs database 120 in addition to blood pressure obtained from spot vital signs measuring devices.

In the example system 500, physiological data obtained on an episodic basis for a patient is sent to the episodic connectivity service module 110. The episodic connectivity service module 110 uses one or more API commands to send the episodic physiological data to the client services module 116. The client services module 116 uses API commands, typically SQL commands, to store the episodic physiological data for the patient in the vital signs database 120.

Figure 6:
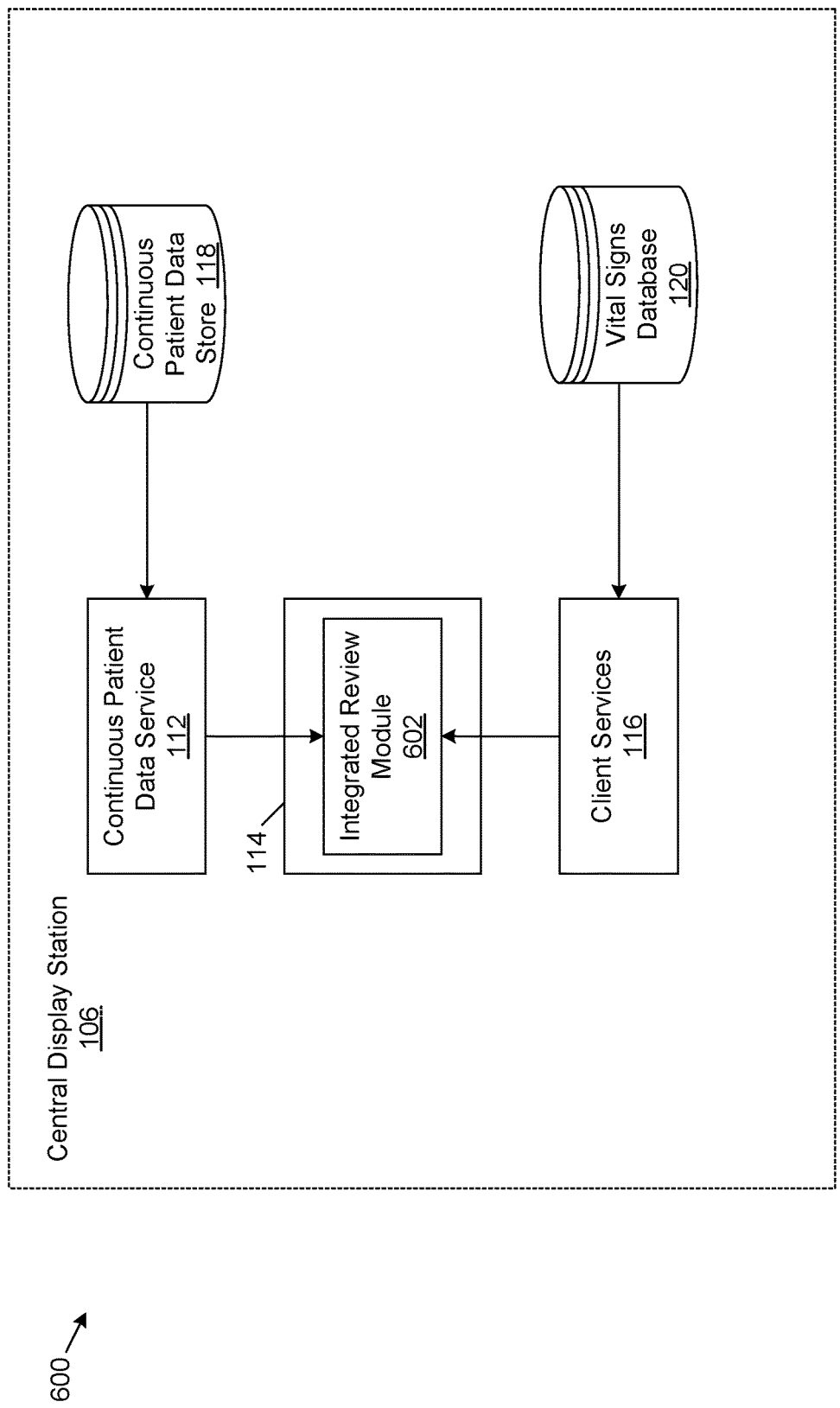
FIG. 6 shows components of the example system of FIG. 1.

FIG. 6 shows an example system 600 that includes components of the system 100 of FIG. 1 used in an integrated review aspect of system 100 for retrieving and displaying continuous and episodic data for a patient. The integrated review aspect of system 100 permits a clinician to display a more detailed view of patient physiological data than is available from a normal display tile, for example from display tile 202. The integrated review aspect of system 100 is more detailed in terms of historical data. The normal display tile generally shows only a current value of the patient physiological data. The integrated review aspect of system 100 may show historical data going back multiple days, thereby permitting a clinician to view more recent data in the context of historical data values.

The system 600 includes an example integrated review module 602 that integrates continuous physiological data stored in the continuous patient data store 118 with episodic physiological data stored in the vital signs database 120. The integrated review module 602 displays the integrated continuous and episodic physiological data for a patient on a detailed display tile of the user interface 200 of the central display station 106. The integrated review module 602 also permits a display of alarms for a patient and provides continuous and episodic physiological data for a patient in graphical timeline and tabular formats.

In system 600, the integrated review module 602 receives physiological data obtained for a patient on a continuous basis from the continuous patient data store 118. A request is made via API commands to the continuous patient data service module 112. The continuous patient data service module 112 uses file system API commands to obtain the continuous physiological data from the continuous patient data store 118 and send the continuous physiological data for the patient to the integrated review module 602.

The integrated review module 602 also receives physiological data obtained for a patient on a spot or episodic basis from the vital signs database 120. A request is made via API commands and a client framework to the client service module 116. The client services module 116 uses database commands, typically SQL commands, to obtain episodic physiological data for the patient from the vital signs database 120 and send the episodic physiological data for the patient to the integrated review module 602.

The integrated review module 602 integrates the physiological data received from the continuous patient data store 118 and the vital signs database 120 and supplies the integrated physiological data to the user interface of the central display station 106. Integrating the physiological data refers to identifying and processing continuous and episodic physiological data with common time positions and presenting the continuous and episodic physiological data for display. Integration may also involve correlating some physiological data from the continuous patient data store 118 and the vital signs database 120.

For example, a pulse rate may have been obtained from a NIBP measurement stored in the vital signs database 120 and from a SPO2 measurement stored in the continuous patient data store 118. The integration results in a display of the pulse rate in a correct time position in relation to other physiological data occurring during a common time period. The integrated physiological data may be displayed on a device detail screen or on one or more review screens, as explained later herein.

Processing the physiological data from the continuous patient data store 118 and the vital signs database 120 also involves up-sampling or down-sampling the physiological data. Large amounts of physiological data may be stored in the continuous patient data stored 118 and the vital signs database 120. For example, physiological data for a patient from one or more physiological sensors may be obtained at short intervals, for example at one second intervals, on a continuous basis. This amount of continuous data can be too much data to be effectively displayed on the user interface of the central display station 106.

For this reason sampling is used. Down-sampling involves displaying only a portion of the data stored in the continuous patient data store 118 or the vital signs database 120. Down-sampling refers to sampling at a higher sampling rate to display less physiological data on a chart or graph. Up-sampling refers to sampling at a lower rate to display more physiological data on the chart or graph. For example, when a clinician wants to see a high-level summary of the physiological data, for example at hour intervals, down-sampling may be used. When a clinician needs to focus on a portion of the physiological data, for example at one second intervals, up-sampling may be used.

The integrated review module 602 typically comprises two layers—a plug-in module and an integrative review service. The plug-in module typically provides a user interface for displaying the one or more review screens. The integrative review service provides application software for integrating and processing the review data. In some embodiments, the user interface functions and the integrative review service both reside on the central display station.

In other embodiments, the integrative review service may reside on a server computer and the plug-in functionality may reside on a laptop or other portable computer. When the plug-in functionality resides on the laptop or other portable computer, the laptop or other portable computer acts as a thin client. A thin client refers to a small application running on the laptop or other portable computer. When physiological data is transferred between the laptop or other portable computer and the server computer, the physiological data transferred comprises sampled physiological data. Performing integration and processing of the physiological data on the server computer and transferring down-sampled physiological data to the laptop or other portable computer significantly reduces the amount of physiological data that needs to be transmitted, improving the user experience and reducing demands on the wireless network that typically interconnects those devices.

Figure 7:
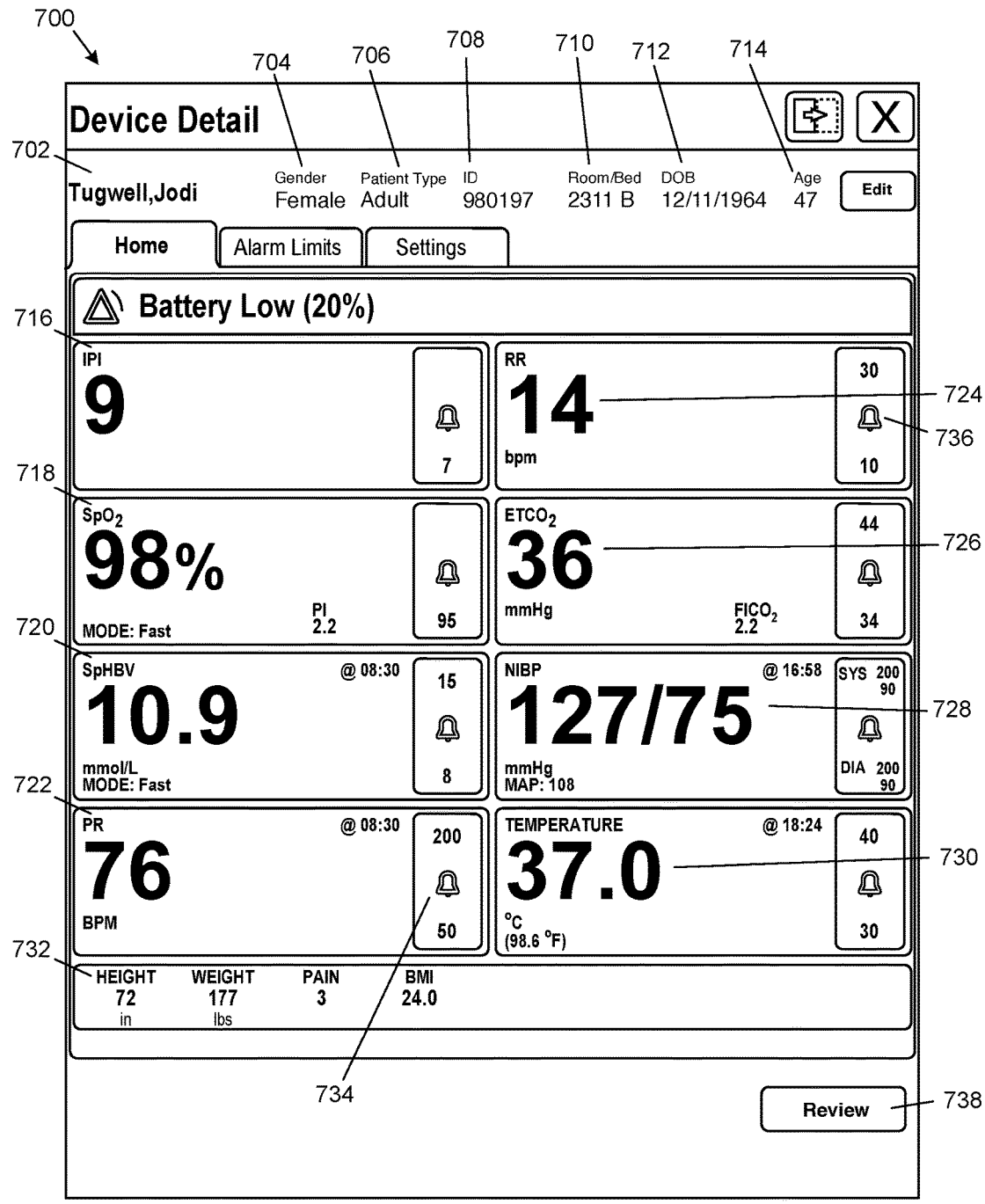
FIG. 7 shows a screen shot of an example device detail screen that includes a display of physiological data for a patient processed by the integrated review module component of FIG. 6.

FIG. 7 shows a screen shot of an example device detail screen 700 that includes a display of physiological data for a patient processed by the integrated review module 602. The device detail screen 700 includes a name 702 of a patient, a gender 704 for the patient, a patient type 706, in this case an adult, a patient ID 708, a room/bed number for the patient, 710, a date of birth 712 for the patient, an age 714 of the patient and a display of physiological parameters for the patient including IPI (integrated pulmonary index) 716, SPO2 (oxygen saturation) 718, SPHBV (venous calibrated total hemoglobin) 720, PR (pulse rate) 722, RR (respiration rate) 724, ETCO2 (end-tidal carbon dioxide) 726, NIBP (non-invasive blood pressure) 728, and temperature 730.

The example device detail screen also includes data 732 such as height, weight, pain indication and BMI (body mass index) for the patient, alarm threshold ranges for the patient such as an alarm threshold range 734 of 50-200 for pulse rate and an alarm threshold range 736 of 10-30 for respiration rate. More or fewer details and physiological parameters may be displayed.

The example device detail screen 700 also includes an example review button 738. When the review button 738 is selected, a review screen is displayed. The review screen permits a clinician to display alarms that have occurred for the patient and tabular or graphical displays of continuous and episodic physiological data for the patient. In addition, the review screen includes controls that permit refinement of the tabular and graphical displays of the continuous and episodic and physiological data for the patient. An example of a graphical display is a timeline showing changes in the continuous and episodic physiological data over time.

Figure 8:
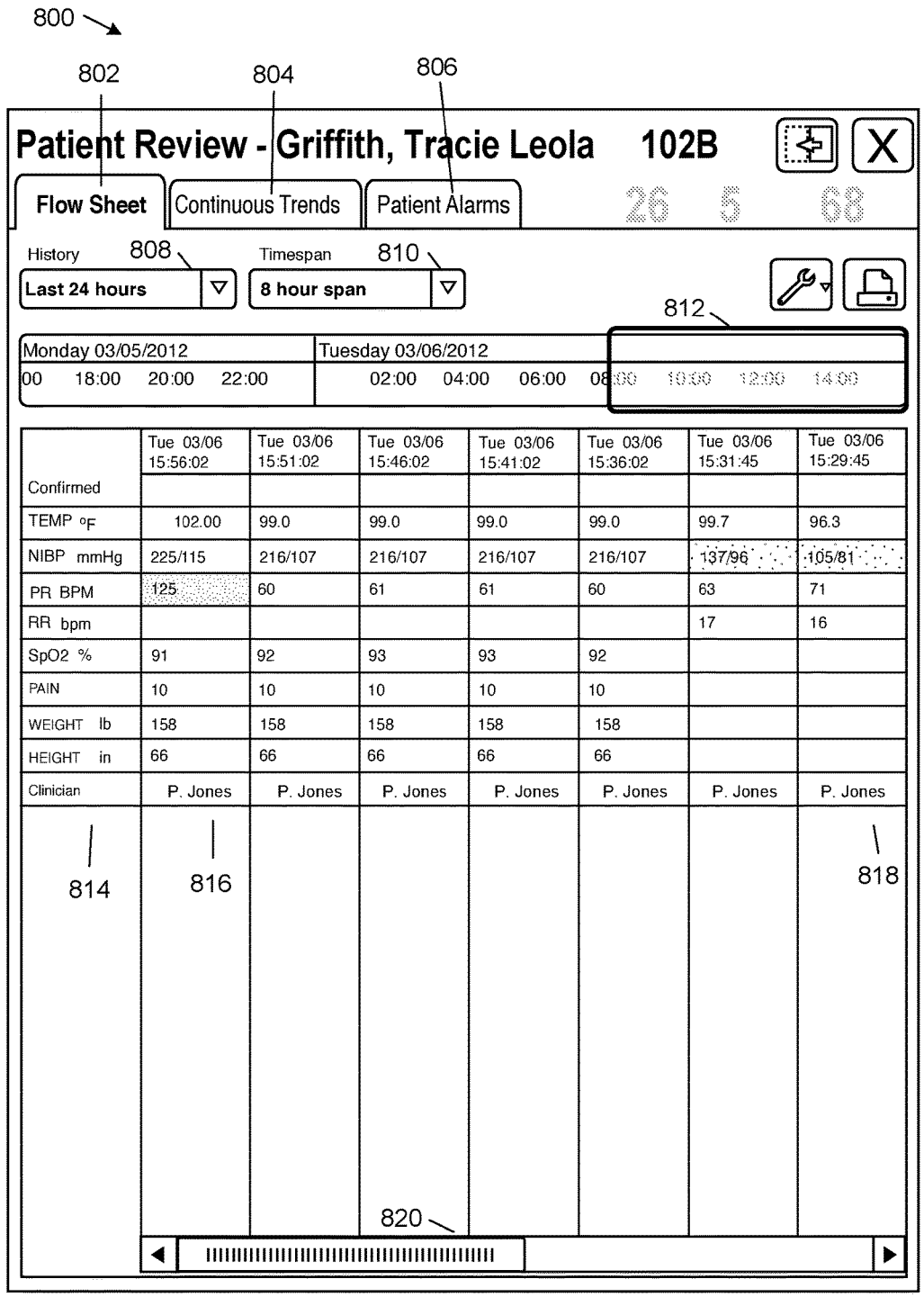
FIG. 8 shows a screen shot of an example patient review screen.

FIG. 8 shows a screen shot of an example review screen 800. The example review screen 800 includes three tabs—a flow sheet tab 802, a continuous trends tab 804 and a patient alarms tab 806. When the example flow sheet tab 802 is selected, trends of episodic physiological data for the patient are displayed. When the example continuous trends tab 804 is selected, trends of continuous physiological data combined with episodic data for the patient are displayed. When the example patient alarms tab 806 is displayed, recent alarms in both continuous and episodic data for the patient are displayed. In review screen 800, the flow sheet tab 802 is selected.

The flow sheet tab 802 includes three controls 808, 810, 812 that permit refinement of the trend episodic physiological data displayed on the review screen 800. History control 808 permits selection of a history time period for the episodic physiological data. The history time period represents a time range for which the episodic physiological data is obtained from a vital signs database, for example from vital signs database 120.

Every entry of episodic physiological data stored in vital signs database 120 includes a timestamp. The history time period represents a range of time for which entries are retrieved from vital signs database 120. As shown in FIG. 8, episodic physiological data is retrieved from the vital signs database 120 for a period of time corresponding to the last 24 hours. Other time periods are possible, including for example 48 hours, 72 hours, 96 hours, seven days, one month and six months.

Timespan control 810 permits selection for a timespan for the display of episodic physiological data for the patient. The timespan represents a range of time that is actually displayed on the review screen 800, in this case 8 hours. By adjusting scroll bar 820, up to 8 hours of trend episodic data may be displayed. Other time spans are possible, for example 1 hour, 2 hours, 4 hours, 8 hours, 12 hours and 24 hours Timespans of 8 hours or 12 hours may be default timespans, corresponding to typical lengths of a nurse's shift.

Time window control 812 shows a time window corresponding to the timespan selected by control 810. For example, the length of control 812 corresponds to a period of 8 hours. A user can move the position of time window control 812 to select other 8 hour time intervals within the history data available, in this example within a 24 hour period.

The trend episodic physiological data displayed in review screen 800 provides example episodic physiological parameters including TEMP, NIBP, PR, SPO2, pain, weight and height. Values of each of these parameters are provided in tabular form for selected times and dates, including a first set of displayed values 816 from 03/06 at 15:56:02 to a last displayed values 818 from 03/06 at 15:29:45.

FIG. 9 shows a screen shot of an example review screen 900 showing trends of continuous physiological data for a patient. In the review screen 900, a continuous trends tab 902 is selected. The review screen 900 includes a history control 904, a timespan control 906 and an interval control 908. The history control 904 permits selection of a history time period for the continuous physiological data. The history time period represents a time range for which the continuous physiological data is obtained from a continuous patient data store, for example from continuous patient data store 118.

Every entry of continuous physiological data stored in continuous patient data store 118 includes a timestamp. The history time period represents a range of time for which entries are retrieved from continuous patient data store 118. As shown in FIG. 9, continuous physiological data is retrieved from the continuous patient data store 118 for a period of time corresponding to the last 24 hours. Other time periods are possible, including for example 48 hours, 72 hours and 96 hours.

Timespan control 906 permits selection for a timespan for the display of continuous physiological data for the patient. The timespan represents a range of time that is actually displayed on the review screen 900, in this case 8 hours. By adjusting scroll bar 914, up to 8 hours of trend episodic data may be displayed. Other time spans are possible.

Interval control 908 permits selection of a frequency for down-sampling continuous data from the continuous patient data store 118. Review screen 900 shows a sampling frequency of 15 minutes, indicating that physiological data for each continuous physiological parameter displayed on review screen 900 is obtained from the continuous patient data store 118 every 15 minutes. If a clinician needed more detailed trend data, a shorter frequency, for example one minute, may be selected. If a clinician wanted less detail, a longer frequency, for example one hour, may be selected Time window control 916 shows a time window corresponding to the timespan selected by interval control 908. For example, the length of time window control 916 corresponds to a period of 8 hours. A user can move the position of control 916 to select other 8 hour time intervals within the history data available, in this example within a 24 hour period.

In review screen 900, continuous physiological data and episodic physiological data are shown in tabular form. Timestamps for trend data are shown in a column labeled 910. The physiological parameters being monitored are shown in a row labeled 912. In this example, the physiological parameters being monitored include temperature (TEMP), non-invasive blood pressure (NIBP), pulse rate (PR), respiration rate (RR), oxygen saturation (SPO2), end-tidal carbon dioxide (ETCO2), integrated pulmonary index (IPI) and total hemoglobin (SPHB). The values for the physiological parameters show trends in these parameters over time.

FIG. 10 shows a screen shot of an example patient alarms screen 1000 for a patient. The patient alarms screen 1000 includes an alarm detail area 1002 that lists alarm events for the patient. A time stamp is provided with each listed alarm, showing a date and time at which the alarm event occurred.

Figure 11:
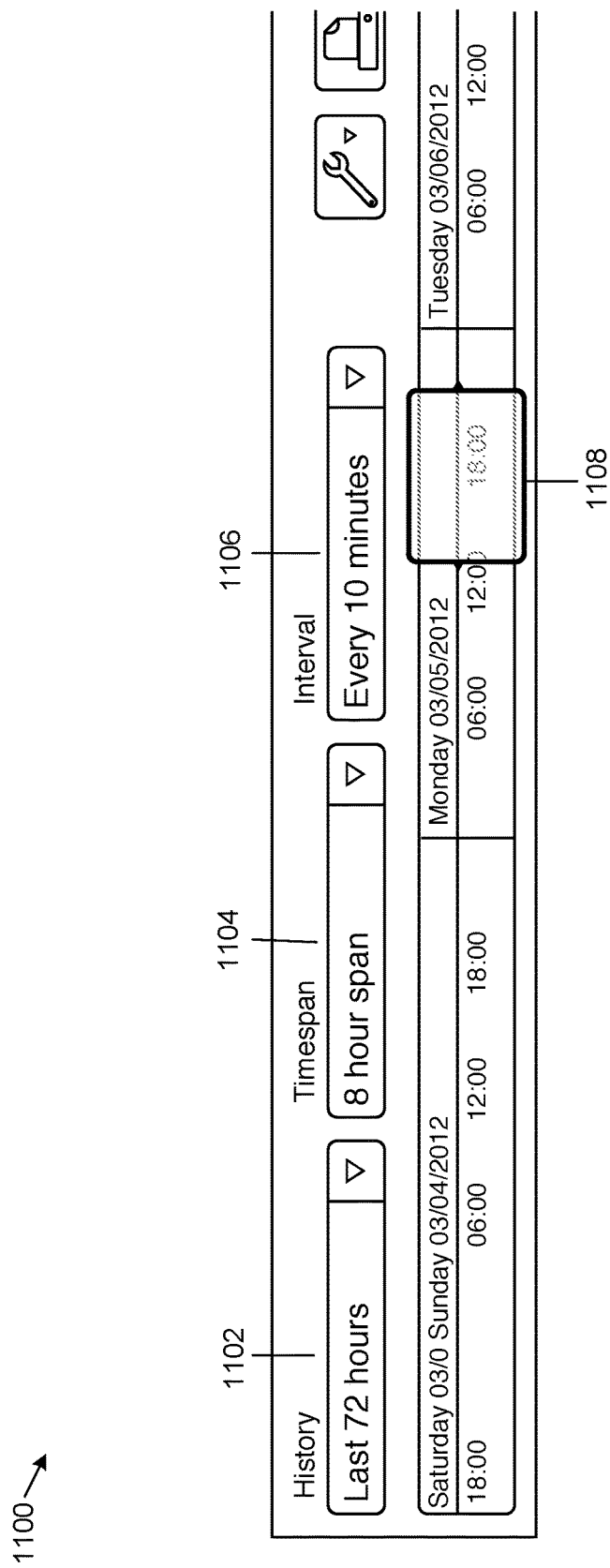
FIG. 11 shows a screen shot of example controls used on the review screens of FIGS. 8 and 9.

FIG. 11 shows example controls 1100 of a review screen for continuous trends in more detail. The controls 1100 include a history control 1102, a timespan control 1104, an interval control 1106, and a time window control 1108. The history control 1102 permits selection of a history time period for continuous physiological data. The history time period represents a time range for which the continuous physiological data is obtained from a continuous patient data store.

The timespan control 1104 permits selection for a timespan for the display of continuous physiological data for the patient. The timespan represents a range of time that is actually displayed on the review screen, in this case 8 hours. The interval control 1106 permits selection of a frequency for sampling continuous data from the continuous patient data store. The time window control 1108 provides selection of a time window within the timespan selected.

Figure 12:
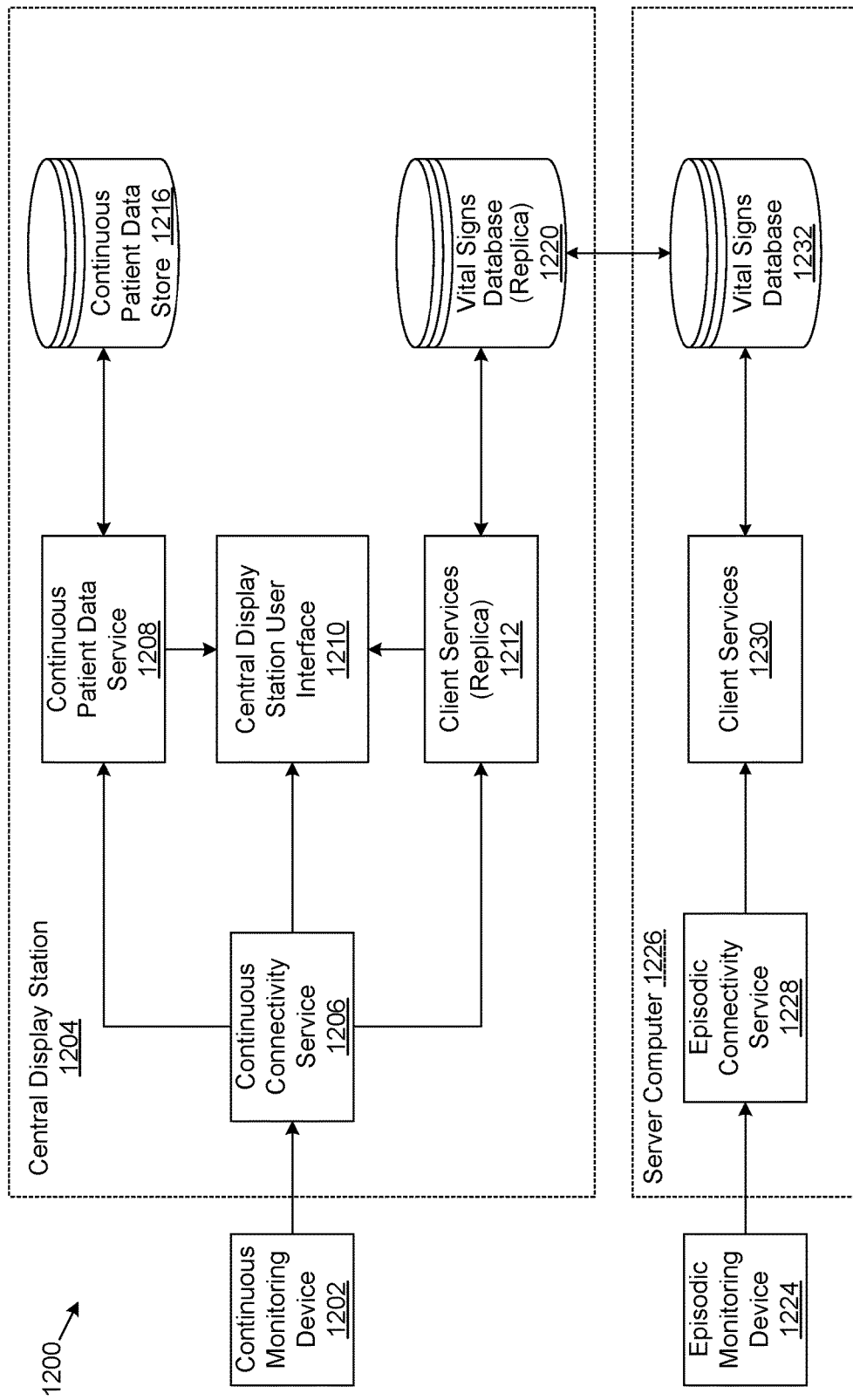
FIG. 12 shows an alternate embodiment for the system of FIG. 1.

FIG. 12 shows an example system 1200 that supports integration of continuous and episodic physiological data for a patient at a central display station and that is an alternate embodiment of system 100 of FIG. 1. In contrast to system 100 where processing and storage for continuous and episodic physiological data are all implemented at central display station 106, in system 1200, the processing and storage of episodic physiological data are implemented at server computer 1226. Server computer 1226 includes episodic connectivity service module 1228, client services module 1230, and vital signs database 1232.

Central display station 1204 includes a replica 1220 of vital signs database 1232 and a replica 1212 of client services module 1230. A TCP connection transfers data between vital signs database 1232 and vital signs database replica 1220. Episodic physiological data displayed on a user interface 1210 of central display station 1204 is obtained from vital signs database replica 1220, which is synchronized via the TCP connection with vital signs database 1232 on server computer 1226.

As discussed in regard to system 100, central display station 1204 in system 1200 includes a connectivity services module 1206 that sends continuous physiological data to a patient data store 1216 via a continuous patient data service module 1208. The central display station 1204 also includes a central display station user interface 1210 that receives continuous physiological data from the connectivity services module 1206 and displays the continuous physiological data in real time on a user interface of the central display station user interface 1210. The central display station user interface module 1210 also includes an integrated review module that includes the same functionality of integrated review module 602.

Figure 13:
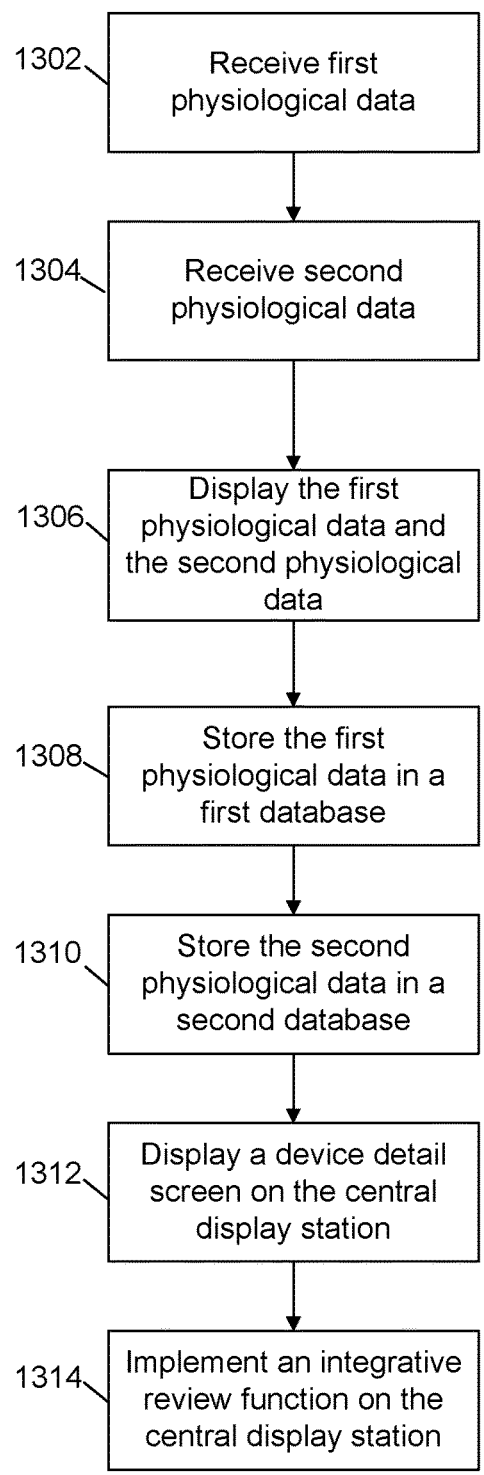
FIG. 13 shows an example flowchart of a method for providing an integrated display of continuous and episodic physiological data for a patient on a medical display station.

FIG. 13 shows an example flowchart for a method 1300 for providing an integrated display of continuous and episodic physiological data for a patient on a medical display station. At operation 1302, physiological data for a patent is received from a medical monitoring device that monitors one or more physiological parameters for the patient on a continuous basis. Examples of physiological parameters that are monitored on a continuous basis include pulse rate, respiration rate and end-tidal carbon dioxide. An example of a medical monitoring device that monitors physiological parameters for a patient on a continuous basis is the Welch Allyn 1500 Patient Monitor.

At operation 1304, physiological data for a patent is received from a medical monitoring device that monitors one or more physiological parameters for the patient on an episodic basis. Examples of physiological parameters that are monitored on an episodic basis include temperature and non-invasive blood pressure. An example of a medical monitoring device that monitors physiological parameters for a patient on an episodic basis is the Connex® Vital Signs Monitor from Welch Allyn, Inc.

At operation 1306, both the continuous and episodic physiological data received for the patient are displayed in real time on a display screen of a central display station, for example central display station 106. The continuous and episodic physiological data is integrated and displayed together on the same display screen.

At operation 1308, the continuous physiological data is stored in a continuous patient data store, for example continuous patient data store 118. At operation 1310, the episodic physiological data is stored in a vital signs database, for example vital signs database 120.

At operation 1312, a device detail screen is displayed on the central display station 106. The device detail screen is displayed when a user clicks on a display tile, for example display tile 202 on the user interface 200 of the central display station 106. Physiological data for the patient is obtained from the continuous patient data store 118 and the vital signs database 120 and displayed on the display tile 202.

At operation 1314, an integrated review function is implemented on the central display station. In examples, the integrated review function is implemented by clicking on a review button on the display tile 202. The integrated review function permits the display of patient alarms and of trend data for continuous and episodic physiological data for the patient.

Figure 14:
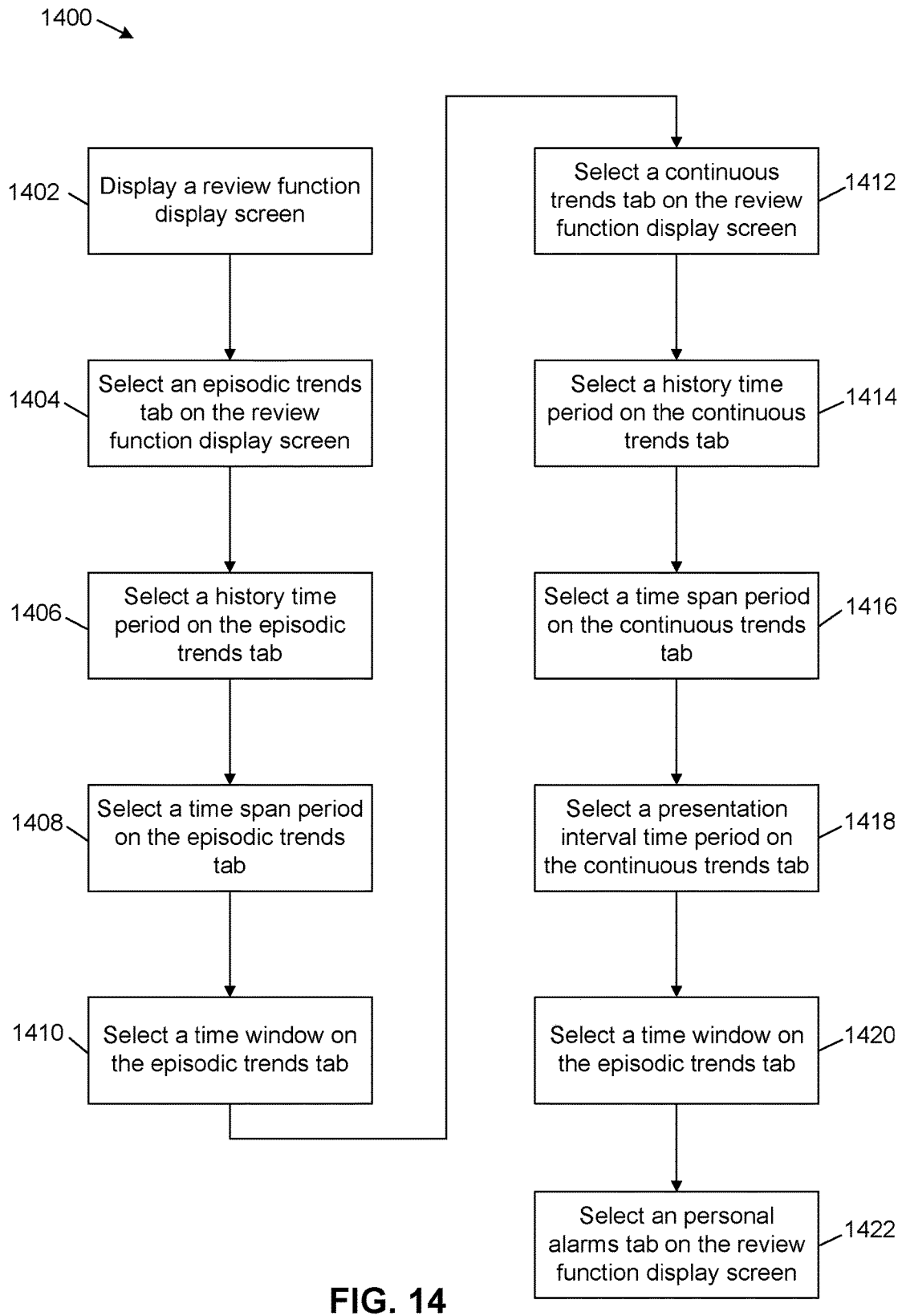
FIG. 14 shows an example flowchart of a method for implementing an integrated review function.

FIG. 14 shows an example a flow chart for a method 1400 for implementing an integrated review function. At operation 1402, a review function display screen is displayed on the central display station 106. An example review function display screen is provided by review screen 800, shown in FIG. 8.

At operation 1404, an episodic review trends tab is selected on the review function display screen. On review screen 800, the episodic review trends tab corresponds to flow sheet tab 802. Selection of the flow sheet tab 802 results in a display of trends in episodic physiological data, as shown in review screen 800.

At operation 1406, a history time period is selected on the review function display screen. On review screen 800, control 808 is used to select the history time interval. The history time period represents a time range for which episodic physiological data is obtained from vital signs database 120. A history time period of 24 hours is shown as being selected on review screen 800.

At operation 1408, a time span period is selected on the review function display screen. On review screen 800, control 810 is used to select the time span period. The timespan represents a range of time that is actually displayed on the review screen 800, in this case 8 hours. By adjusting scroll bar 820, up to 8 hours of trend episodic data may be displayed.

At operation 1410, a time window is selected on the review function display screen. On review screen 800, control 812 is used to select the time window. The time window indicates a length of time corresponding to the timespan selected by control 810. For example, the length of control 812 corresponds to a period of 8 hours. A user can move the position of control 812 to select other 8 hour time intervals within the history data available, in this example within a 24 hour period.

At operation 1412, a continuous trends tab, for example continuous trends tab 804, is selected on the review function display screen. Selection of the continuous trends tab displays a continuous trends review screen, showing trends in continuous physiological data for a patient. An example continuous trends review screen is shown on review screen 900 in FIG. 9.

At operation 1414, a history time period is selected on the continuous trends tab. On review screen 900, history control 904 is used to select the history time interval. The history time period represents a time range for which episodic physiological data is obtained from vital signs database 120. A history time period of 24 hours is shown as being selected on review screen 900.

At operation 1416, a time span period is selected on the continuous trends tab. On review screen 900, timespan control 906 is used to select the time span period. The timespan represents a range of time that is actually displayed on the review screen 800, in this case 8 hours. By adjusting vertical scroll bar 914, up to 8 hours of trend episodic data may be displayed.

At operation 1418, a presentation period time interval is selected on the continuous trends tab. On review screen 900, interval control 908 permits selection of a presentation period time interval. The presentation time period corresponds to a sampling frequency for sampling continuous data from the continuous patient data store 118. Review screen 900 shows a sampling frequency of 15 minutes, indicating that physiological data for each continuous physiological parameter displayed on review screen 900 is obtained from the continuous patient data store 118 every 15 minutes.

At operation 1420, a time window is selected on the review function display screen. On review screen 900, control 916 is used to select the time window. The time window indicates a length of time corresponding to the timespan selected by control 908. For example, the length of control 916 corresponds to a period of 8 hours. A user can move the position of control 916 to select other 8 hour time intervals within the history data available, in this example within a 24 hour period.

At operation 1422, a patient alarms tab is selected on the review function display screen. On review screen 800, patient alarms tab 806 is selected. Selecting the patient alarms tab displays a patient alarms screen. An example patient alarms screen is patient alarms screen 1000, shown in FIG. 9. The patient alarms screen 1000 provides alarm information for the patient and highlights the alarm in a highlighting color, typically red or yellow.

Figure 15:
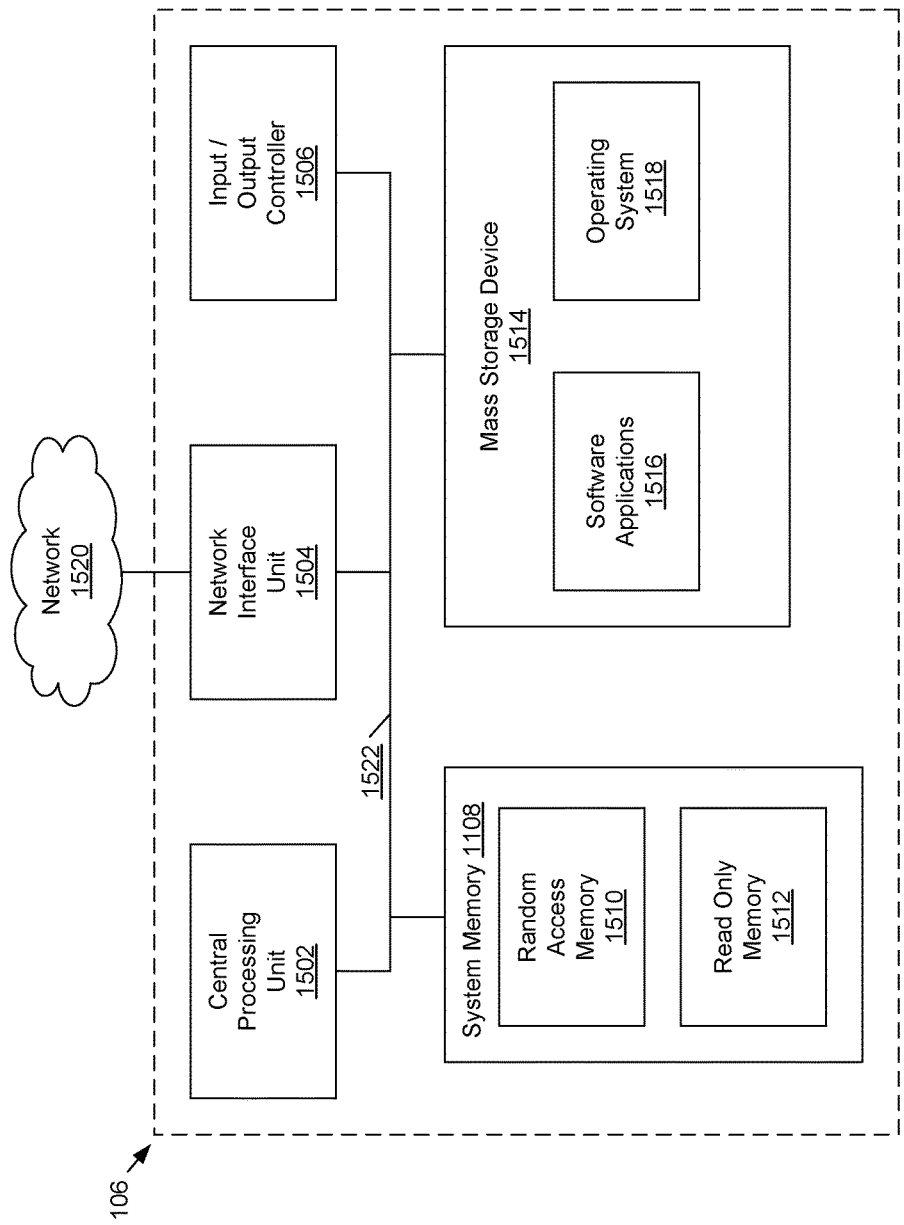
FIG. 15 shows example physical components of the central display station of FIG. 1.

FIG. 15 illustrates example physical components of the central display station 106. As illustrated in the example of FIG. 15, the central display station 106 includes at least one central processing unit ("CPU") 1502, a system memory 1508, and a system bus 1522 that couples the system memory 1508 to the CPU 1502. The system memory 1508 includes a random access memory ("RAM") 1510 and a read-only memory ("ROM") 1512. A basic input/output system contains the basic routines that help to transfer information between elements within the central display station 106, such as during startup, is stored in the ROM 1512. The central display station 110 further includes a mass storage device 1514. The mass storage device 1514 is able to store software instructions and data.

The mass storage device 1514 is connected to the CPU 1502 through a mass storage controller (not shown) connected to the bus 1522. The mass storage device 1514 and its associated computer-readable data storage media provide non-volatile, non-transitory storage for the central display station 110. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the central display station 110.

According to various embodiments of the invention, the central display station 110 may operate in a networked environment using logical connections to remote network devices through the network 1520, such as a local network, the Internet, or another type of network. The central display station may connect to the network 1520 through a network interface unit 1504 connected to the bus 1522. It should be appreciated that the network interface unit 1504 may also be utilized to connect to other types of networks and remote computing systems. The central display station 110 also includes an input/output controller 1506 for receiving and processing input from a number of other devices, including a keyboard, a mouse, a touch user interface display screen, or another type of input device. Similarly, the input/output controller 1506 may provide output to a touch user interface display screen, a printer, or other type of output device.

As mentioned briefly above, the mass storage device 1514 and the RAM 1510 of the central display station 110 can store software instructions and data. The software instructions include an operating system 1518 suitable for controlling the operation of the central display station 110. The mass storage device 1514 and/or the RAM 1510 also store software instructions, that when executed by the CPU 1502, cause the central display station 110 to provide the functionality of the central display station 110 discussed in this document. For example, the mass storage device 1514 and/or the RAM 1510 can store software instructions that, when executed by the CPU 1502, cause the central display station 110 to display the user interface 200 screen and other screens.

The various embodiments described above are provided by way of illustration only and should not be construed to limiting. Various modifications and changes that may be made to the embodiments described above without departing from the true spirit and scope of the disclosure.

What is claimed is:

1. A method for displaying medical data, the method comprising:
    receiving first physiological data from a first medical monitoring device, the first physiological data being obtained on a continuous basis;
    receiving second physiological data from a second medical monitoring device, the second physiological data being obtained on a non-continuous basis;
    displaying the first physiological data and the second physiological data on a display tile of a display screen of a central display station;
    allowing selection of a review function button; and
    as a result of receiving selection of the review function button:
        displaying a first trend display for the first physiological data being obtained on the continuous basis, the first trend display being a first table including a plurality of data points from the first physiological data; and
        displaying a second trend display for the second physiological data being obtained on the non-continuous basis, the second trend display being a second table including a plurality of data points from the second physiological data.

2. The method of claim 1, wherein the first physiological data is obtained via a first workflow and the second physiological data is obtained via a second workflow, the first workflow being a workflow in which the first physiological data is obtained on a continuous basis, the second workflow being a spot workflow in which the second physiological data is obtained on a non-continuous basis.

3. The method of claim 2, wherein a portion of the second physiological data is obtained via the first workflow.

4. The method of claim 1, wherein the first physiological data and the second physiological data are obtained from a plurality of patients.

5. The method of claim 1, wherein the central display station is centrally located within a care unit of a caregiving facility.

6. The method of claim 1, wherein the first window includes detailed physiological data for a patient.

7. The method of claim 1, further comprising:
    selecting a first display tile on the display screen, the first display tile corresponding to a first patient, the selection of the first display tile causing a first window to be displayed on the display screen;
    obtaining third physiological data for the first patient from a first database, the third physiological data being physiological data obtained on a continuous basis;
    obtaining fourth physiological data for the first patient from a second database, the fourth physiological data being physiological data obtained on a non-continuous basis; and
    displaying the third physiological data and the fourth physiological data in the first window on the display screen, the first window overlapping one or more other display tiles on the display screen, the first window providing a detailed view of the third physiological data and the fourth physiological data.

8. The method of claim 7, further comprising:
    as a result of selecting the review function button, displaying a second window on the display screen, the second window permitting the display of the third physiological data and the fourth physiological data in tabular and in graphical form.

9. The method of claim 8, wherein the second window includes a plurality of tabs, one tab permitting a display of trend data for the third physiological data, a second tab permitting a display of trend data for the fourth physiological data, a third tab permitting a display of personal alarm data for a patient.

10. The method of claim 8, wherein the second window includes a plurality of control buttons, the plurality of control buttons permitting a selection of an amount of physiological data to be displayed on the second window, permitting a selection of a time and date period for the physiological data to be displayed on the second window and permitting a selection of a time interval at which samples of the physiological data are displayed on the second window.

11. The method of claim 1, further comprising:
storing the first physiological data in the first database; and
storing the second physiological data in the second database.

12. The method of claim 11 further comprising opening a display window on the display screen, the display window permitting the display of the first physiological data and the second physiological data in tabular or graphical form.

13. The method of claim 12, further comprising:
receiving the first physiological data from the first database;
receiving the second physiological data from the second database; and
displaying the first physiological data and the second physiological data on a graphical timeline on the display window.

14. The method of claim 12, further comprising:
receiving the first physiological data the first database;
receiving the second physiological data from the second database; and
displaying the first physiological data and the second physiological data in tabular form on the display window.

15. The method of claim 12, wherein the display window includes a plurality of controls that permit selection of a time period for the display of the first and second physiological data.

16. The method of claim 1, further comprising:
receiving third physiological data from a third medical monitoring device, the third physiological data being obtained on a continuous basis;
receiving fourth physiological data from a fourth medical monitoring device, the fourth physiological data being obtained on a non-continuous basis; and
displaying the third physiological data and the fourth physiological data on the display screen of the central display station.

17. An electronic computing device comprising:
a processing unit; and
system memory, the system memory including instructions that when executed by the processing unit cause the electronic computing device to:
receive first physiological data from a first medical monitoring device, the first physiological data being obtained on a continuous basis;
receive second physiological data from a server computer, the second physiological data being obtained on a non-continuous basis;
display the first physiological data and the second physiological data on a display screen of a central display station, the central display station being located centrally within a caregiving facility;
provide a first trend display for the first physiological data being obtained on the continuous basis, the first trend display being a first table including a plurality of data points from the first physiological data;
provide a second trend display for the second physiological data being obtained on the non-continuous basis, the second trend display being a second table including a plurality of data points from the second physiological data;
permit a selection of a time and date period for the second physiological data to be displayed on the second trend display; and
permit a selection of a time interval at which samples of the second physiological data are to be displayed on the second trend display.

18. The electronic computing device of claim 17, further comprising:
store the first physiological data in a first database;
store the second physiological data in a second database;
receive the first physiological data the first database;
receive the second physiological data from the second database;
display the first physiological data and the second physiological data in tabular form on a window on the display screen;
using a control on the display screen to adjust a sampling rate for the first physiological data and for the second physiological data; and
using a control on the display screen to select a time interval for the first physiological data and for the second physiological data.

* * * * *